(12) United States Patent
Kawahara et al.

(10) Patent No.: US 6,693,214 B2
(45) Date of Patent: Feb. 17, 2004

(54) INTERMEDIATE FOR SWEETENER WITH HIGH SWEETNESS AND PROCESS FOR PRODUCING THE SAME

(75) Inventors: Shigeru Kawahara, Kawasaki (JP); Kenichi Mori, Kawasaki (JP); Kazutaka Nagashima, Kawasaki (JP); Tadashi Takemoto, Kawasaki (JP)

(73) Assignee: Ajinomoto Co., Inc., Tokyo (JP)

( * ) Notice: Subject to any disclaimer, the term of this patent is extended or adjusted under 35 U.S.C. 154(b) by 74 days.

(21) Appl. No.: 10/150,106

(22) Filed: May 20, 2002

(65) Prior Publication Data
US 2003/0216592 A1 Nov. 20, 2003

Related U.S. Application Data

(63) Continuation of application No. PCT/JP00/07913, filed on Nov. 9, 2000.

(30) Foreign Application Priority Data

Nov. 18, 2000 (JP) ........................................ 2000-328100

(51) Int. Cl.[7] ........................ C07C 47/52; C07C 47/54; C07C 47/542; C07C 33/18; C07C 63/64
(52) U.S. Cl. ........................ 562/405; 568/425; 568/715
(58) Field of Search .................. 420/425; 568/700, 568/715, 812, 840, 425; 562/400, 405

(56) References Cited

U.S. PATENT DOCUMENTS 5,705,704 A    1/1998  Brion et al.
6,221,907 B1   4/2001  Bernard et al.

FOREIGN PATENT DOCUMENTS

JP   WO97/34865   9/1997
JP   WO99/52937   10/1999

OTHER PUBLICATIONS

U.S. patent application Ser. No. 10/117,205, Kawahara et al., filed Apr. 8, 2002.
U.S. patent application Ser. No. 10/295,997, Mori et al., filed Nov. 18, 2002.
U.S. patent application Ser. No. 10/150,106, Kawahara et al., filed May 20, 2002.
U.S. patent application Ser. No. 10/091,500, Amino et al., filed Mar. 7, 2002.
U.S. patent application Ser. No. 10/117,196, Nagashima et al., filed Apr. 8, 2002.
U.S. patent application Ser. No. 10/197,808, Mori et al., filed Jul. 19, 2002.
U.S. patent application Ser. No. 10/108,426, Nagashima et al., filed Mar. 29, 2002.
U.S. patent application Ser. No. 10/286,840, Kawahara et al., filed Nov. 4, 2002.

Primary Examiner—Johann Richter
Assistant Examiner—Karl Puttlitz
(74) Attorney, Agent, or Firm—Oblon, Spivak, McClelland, Maier & Neustadt, P.C.

(57) ABSTRACT

The present invention relates to a 3-substituted-phenyl-3-merthylbutyric acid and 3-substituted-phenyl-3-merthylaldehyde derivatives, which are useful in the production of N-[N-[3-(3-hydroxy-4-methoxyphenyl)-3-methylbutyl]-L-α-aspartyl]-L-phenylalanine 1-methyl ester, which is a sweetener with high sweetening potency.

8 Claims, No Drawings

INTERMEDIATE FOR SWEETENER WITH HIGH SWEETNESS AND PROCESS FOR PRODUCING THE SAME

CROSS-REFERENCE TO RELATED APPLICATION

The present application is a Continuation Application of PCT/JP00/07913 filed on Nov. 9, 2000, the contents of which are incorporated herein by reference.

FIELD OF THE INVENTION

The present invention relates to a 3-substituted-phenyl-3-merthylbutyric acid and 3-substituted-phenyl-3-methylaldehyde derivatives, which are useful in the production of N-[N-[3-(3-hydroxy-4-methoxyphenyl)-3-methylbutyl]-L-α-aspartyl]-L-phenylalanine 1-methyl ester, which is a sweetener with high sweetening potency.

BACKGROUND OF THE INVENTION

In recent years, as eating habits have changed dramatically, excessive weight gain caused by the increasing amounts of sugar found in foods have resulted in health related problems. Accordingly, the development of a low-calorie sweetener (sweetening agent) that replaces sugar has been strongly in demand. An example of such a low-calorie sweetener that is commonly used is aspartame, which is safe and effective for providing a high level of sweetness. However, aspartame is somewhat unstable.

To solve these problems, an —[N-[3-(3-hydroxy-4-methoxyphenyl)-3-methylbutyl]-L-α-aspartyl]-L-phenylalanine 1-methyl ester shown below has been found, which is not only highly stable but is also far better with respect to the sweetening potency it imparts.

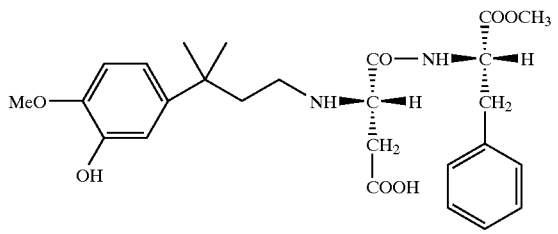

To make the N-[N-[3-(3-hydroxy-4-methoxyphenyl)-3-methylbutyl]-L-α-aspartyl]-L-phenylalanine 1-methyl ester a process of reductively alkylating a β-O-benzyl-α-L-aspartyl-L-phenylalanine methyl ester with a 3-(3-benzyloxy-4-methoxyphenyl)-3-methylbutyl aldehyde followed by removing the benzyl group of a protecting group therefrom has been provided previously by the present inventors. However, in this process, the aldehyde, which is used as an intermediate in the process, requires 7 reaction steps to be synthesized from the 3-hydroxy-4-methoxy acetophenone, which is used as the starting material. This 7-step reaction scheme is shown in the Reaction Process 1 below. Therefore, from the point of industrial profitability, such a reaction is not desirable.

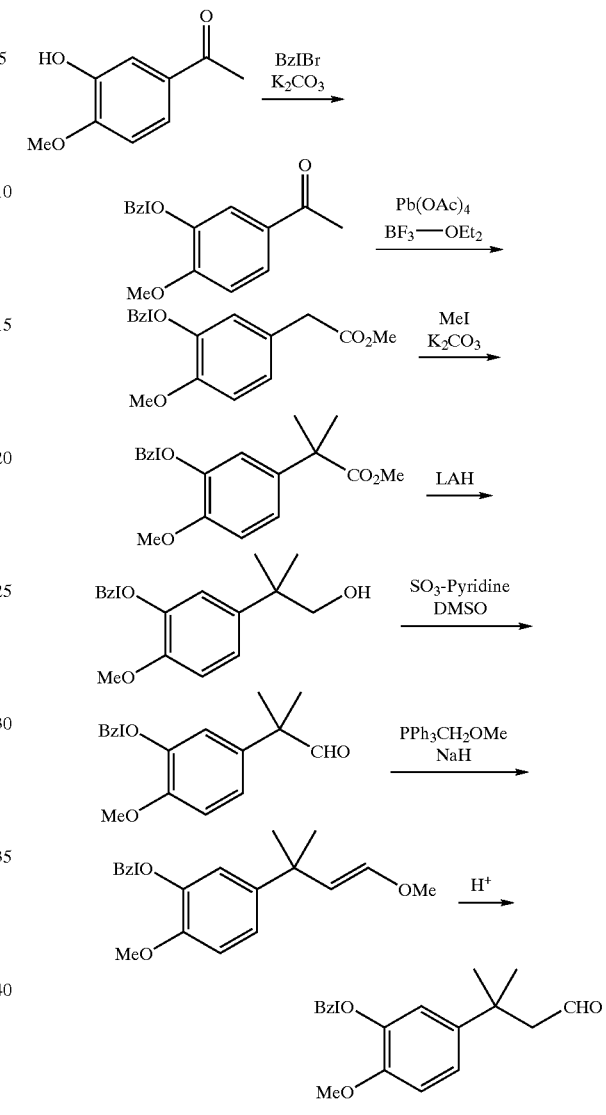

In view of this problem, there is a need in the art for a process for producing industrially and easily the aspartyl dipeptide ester derivative described above.

Therefore, to solve this problem, the present inventors set out to provide processes for industrially and efficiently producing the N-[N-[3-(3-hydroxy-4-methoxyphenyl)-3-methylbutyl]-L-α-aspartyl]-L-phenylalanine 1-methyl ester; and novel intermediate compounds useful in such production processes.

SUMMARY OF THE INVENTION

The present inventors have studied earnestly to solve the above problem, and as a result succeeded in newly synthesizing a 3-(3-hydroxy-4-methoxyphenyl)-3-methylbutyl aldehyde and found that the compound is extremely useful as an intermediate for the production of the N-[N-[3-(3-hydroxy-4-methoxyphenyl)-3-methylbutyl]-L-α-aspartyl]-L-phenylalanine 1-methyl ester. Further, the inventors have discovered an efficient process for producing the compound, which is shown in the following reaction process 2.

[Reaction Process 2]

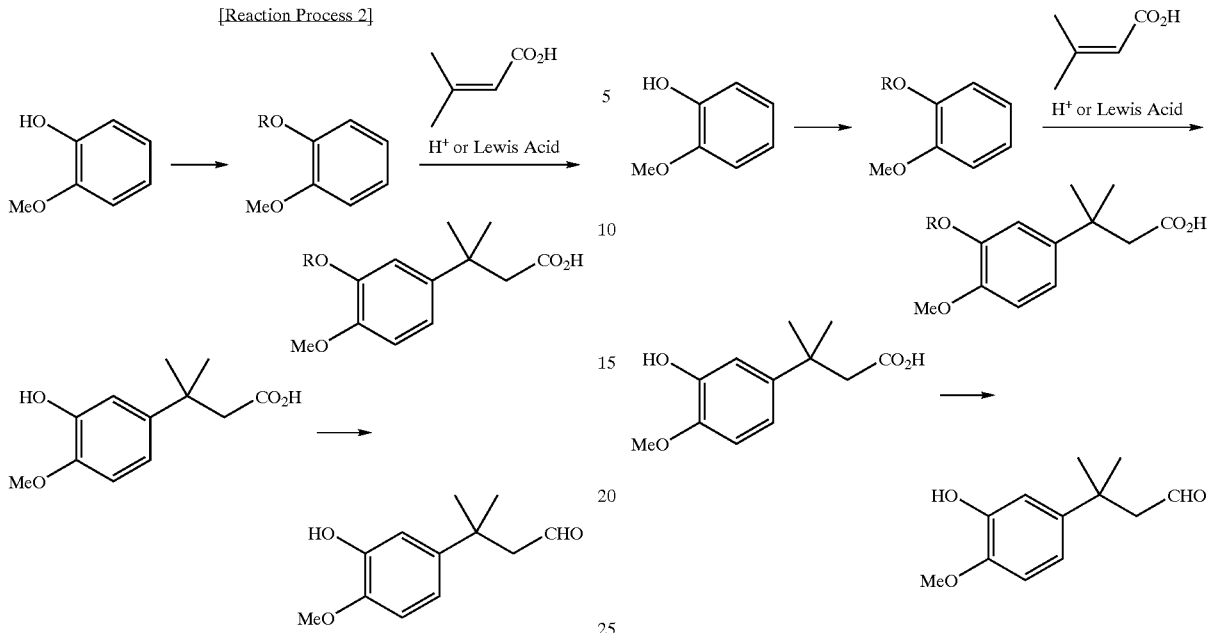

Therefore, an object of the present invention is to provide a process for producing compounds of formula (2):

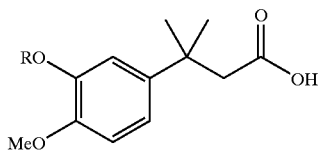

(2)

Another object of the present invention is produce 3-(3-hydroxy-4-methoxyphenyl)-3-methylbutyric acid using the above compound of formula (2).

Another object of the present invention is to provide a process for producing 3-(3-hydroxy-4-methoxyphenyl)-3-methylbutyl aldehyde with the 3-(3-hydroxy-4-methoxyphenyl)-3-methylbutyric acid.

Another object of the present invention is to provide a process for producing N-[N-[3-(3-hydroxy-4-methoxyphenyl)-3-methylbutyl]-L-α-aspartyl]-L-phenylalanine 1-methyl ester with the 3-(3-hydroxy-4-methoxyphenyl)-3-methylbutyl aldehyde.

Another object of the present invention is a compound representated by formula (3):

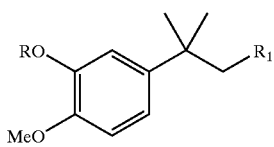

(3)

DETAILED DESCRIPTION OF THE INVENTION

In the process for producing 3-(3-hydroxy-4-methoxyphenyl)-3-methylbutyric acid, as depicted in the "Reaction Process 2" shown below the following disclosure is provided:

To protect the hydroxyl group in a 2-methoxy phenol, the 2-methoxy phenol can be converted to a hydroxyl-protective derivative of 2-methoxy phenol represented by formula (1) (where R is a sulfonyl-type protecting group and Me is a methyl group) by forming a sufonic acid ester from the 2-methoxy phenol, which process may be conducted as described in PROTECTIVE GROUPS IN ORGANIC SYNTHESIS (1991, JOHN WILEY & SONS. INC. NEW YORK), p.168–170, which is incorporated herein by reference.

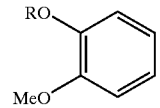

(1)

The reaction of 2-methoxy phenol with the corresponding sulfonic acid anhydride or sulfonic acid chloride can be performed in the presence of a base. An example of a hydroxyl protecting group can be represented by the formula: —$SO_2$—R' as the sulfonyl type-protecting group. R' can be a branched chain or a straight chain (linear) alkyl group having 1 to 10 carbon atoms, which may have one or more substituent groups; an aryl group having 6 to 15 carbon atoms, which may have one or more substituent groups; and an aralkyl group having 7 to 20 carbon atoms, which may have one or more substituent groups. Preferably, the alkyl group(s) have from 1 to 3 carbon atoms. The alkyl group and/or the aralkyl group may be have a fluorine atom wherein one or more of the hydrogen atoms is replaced by fluorine atom(s). For example, a part or a whole of the alkyl group may be a fluoroalkyl group.

Examples of substituents on the alkyl and/or aralkyl include nitro group(s), halogen atom(s) (e.g, Cl, Br, F), and trialkyl ammonium group(s).

The R group, which is a sulfonyl type protecting group, may be, but not limited to, the following: a benzene sulfonyl group (—$SO_2$—$C_6H_5$), a p-toluene sulfonyl group (—$SO_2$—$C_6H_4$—$CH_3$), a p-bromobenzene sulfonyl group (—$SO_2$—$C_6H_4$—Br), a p-nitrobenzene sulfonyl group (—$SO_2$—$C_6H_4$—$NO_2$), a methane sulfonyl group (—SO$_2$—CH$_3$), an ammonioalkane sulfonyl group (—SO$_2$—(CH$_2$)$_n$N(CH$_3$)$_3$$^+$) (n=0 to 6), a trifluoromethane sulfonyl group (—SO$_2$—CF$_3$), a nonafluorobuthane sulfonyl group (—SO$_2$—C$_4$F$_9$), a 2,2,2-trifluoroethane sulfonyl group (—SO$_2$—CH$_2$—CF$_3$). Preferably, R is a methane sulfonyl group, a trifluoromethane sulfonyl group, or a p-toluene sulfonyl group.

The reaction of a hydroxyl-protective derivative of 2-methoxy phenol represented by formula (1) with a 3-methylcrotonic acid can be conducted without a solvent, or conducted in an organic solvent with an acid coexistent. The organic solvent can be any solvent which is inactive with the substrate, with an acid and with a reaction product in the reaction. Examples of such solvents include, methylene chloride, chloroform, and nitrobenzene.

When an acid is used, the acid to be used can be a proton acid (H$^+$), such as sulfuric acid, para (p-)toluenesulfonic acid and hydrogen chloride, a Lewis acid (L.A.), such as aluminum chloride, and titanium tetrachloride. Plural acids can also be employed, respectively in the proton acid or Lewis acid. A proton acid can also be used in combination with a Lewis acid, such as combination of hydrogen chloride with aluminum chloride. In a preferred embodiment, the acid is fixed firmly onto the surface of a solid phase thereby simplifying the process. Preferred acids include, aluminum chloride, titanium tetrachloride and sulfuric acid.

The amount of acid to be employed is not limited particularly, however, an excess of acid relative to the 3-methylcrotonic acid, will allow the reaction to be completed in a shorter time. However, preferably the amount of acid relative to the 3-methylcrotonic acid is in an amount of not more than 5 molar equivalents, more preferably not more than 3 molar equivalents, and further more preferably from 0.1 to 3 molar equivalents.

The amount of the hydroxyl-protective derivative of 2-methoxy phenol represented by formula (1) relative to the 3-methylcrotonic acid is not limited, however, preferably at least 0.5 molar equivalents or more, more preferably 1 molar equivalents or more, and further more preferably 1 to 10 molar equivalents or so, is used relative to the 3-methylcrotonic acid.

There is no particular limitation on the reaction temperature, however, the higher the reaction temperature, the more secondary reactions occur; on the other hand, at a low temperature, the reaction speed becomes extremely slow. Therefore, a temperature of from about 20 to about 180° C. is preferred, and more preferably a temperature of about 30 to about 100° C.

To obtain a 3-(3-hydroxy-4-methoxyphenyl)-3-methylbutyric acid by decomposing a sulfonic acid ester of 3-substituted-phenyl-3-methylbutyric acid represented formula (2), the reaction can be performed under basic conditions. The basic material to be employed is not particularly limited, but is preferably chosen from one or more of a metal hydroxide such as sodium hydroxide, and/or potassium hydroxide. The amount of basic material is also not limited but it is preferred that the basic material be included in an amount of about 1 molar equivalent or more (1 mole or more).

When a solvent is used in the reaction, any solvent can be used as described above. However, when a metal hydroxide such as sodium hydroxide, potassium hydroxide and the like is employed, the solvent(s) preferably also contains at least one of alcohols, such as methanol, ethanol and isopropyl alcohol; and water.

The reaction temperature for removing the protective sulfonic acid ester can be performed at any temperature. However, when a higher temperature is employed, the reaction can be completed in a shorter time. Preferably, a temperature of about 20 to about 150° C., and more preferably about 40 to about 100° C. may be used.

The aldehyde form of 3-(3-hydroxy-4-methoxyphenyl)-3-methylbutyric acid can be produced by converting the carboxyl group in the carboxylic acid into a formyl group.

The 3-(3-hydroxy-4-methoxyphenyl)-3-methylbutyric acid obtained in the above reaction may be directly reduced into the corresponding formyl group from the carboxyl group. Preferably, the reaction is performed as described in Chemistry Letters, issued in 1998, Nov., p.1143–1144 (which is incorporated herein by reference) whereby the starting material can be converted into the 3-(3-hydroxy-4-methoxyphenyl)-3-methylbutyl aldehyde. This process involves reducing the 3-(3-hydroxy-4-methoxyphenyl)-3-methylbutyric acid with hydrogen in an organic solvent together with added pivalic acid anhydride, palladium acetate, and triphenylphosphine derivative.

In this reaction any organic solvent may be employed provided it is inactive with the starting material, a catalyst and a product in the reaction. Examples of solvents that can be used include acetone, tetrahydrofuran, and toluene.

The amount of pivalic acid anhydride to be used is at least an equimolar (equimole) quantity or more of pivalic acid anhydride relative to the 3-(3-hydroxy-4-methoxyphenyl)-3-methylbutyric acid; preferably, about 1 to about 5 times molar (moles) quantity of pivalic acid anhydride to the 3-(3-hydroxy-4-methoxyphenyl)-3-methylbutyric acid.

The triphenylphosphine derivative can be triphenylphosphine, tritolylphosphine, or similar derivatives. The palladium acetate and the triphenylphosphine derivative are employed as the catalyst, and therefore, only some mole % is needed.

The reaction can be performed at any temperature, preferably a temperature range of about 40 to about 100° C., and more preferably a temperature of about 60 to about 80° C. At the higher temperatures, the reaction may be promoted, and can be finished (completed) in a shorter time.

In other embodied methods of forming a 3-(3-hydroxy-4-methoxyphenyl)-3-methylbutyl aldehyde, the 3-substituted-phenyl-3-methylbutyric acid represented by formula (2) the following two processes are described.

Process 1:

As shown in the following reaction scheme, the carboxyl group in the 3-substituted-phenyl-3-methylbutyric acid represented by formula (2) is completely reduced to a hydroxymethyl group, and then the hydroxymethyl group is partially oxidized to form a formyl group. In this case, the reduction—partial oxidation reaction can be conducted as described in the Journal of Organic Chemistry, vol. 48, No. 25, p. 5043–5048, 1983, which is incorporated by reference.

The sulfonic acid ester is deprotected; and then the acetyl, such as a dimethyl acetal group, protecting the formyl group is removed through acidic hydrolysis, whereby the 3-(3-hydroxy-4-methoxyphenyl)-3-methylbutyl aldehyde can be obtained.

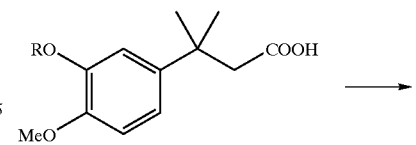

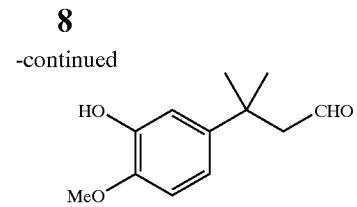

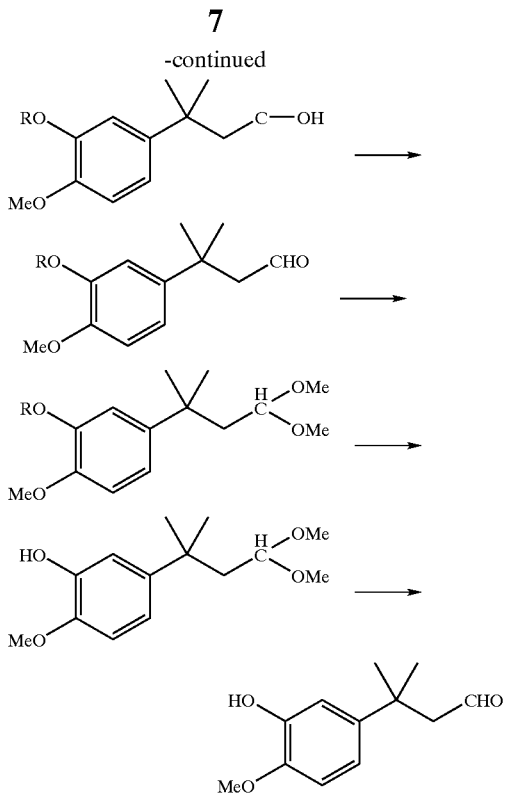

Process 2:

As shown in the following reaction route, the carboxyl group in the 3-substituted-phenyl-3-methylbutyric acid represented by the general formula (2) can be reduced from the carboxyl group to the formyl group, and the formyl group can be protected with an acetal group, such as dimethyl acetal group, and then the sulfonic acid ester is decomposed, and subsequently, the acetal group is removed through acidic hydrolysis whereby the 3-(3-hydroxy-4-methoxyphenyl)-3-methylbutyl aldehyde can be obtained.

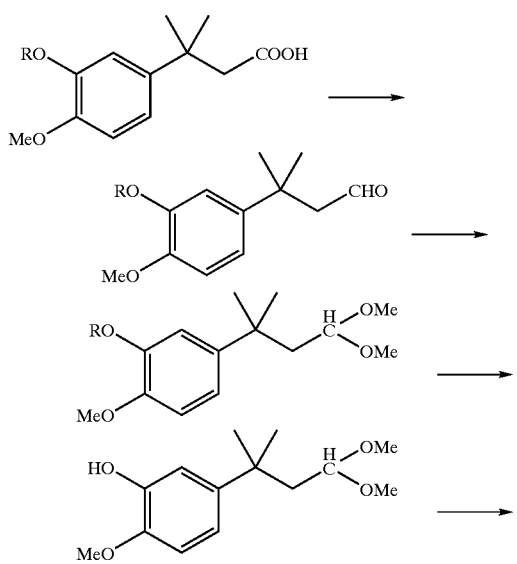

Between these two processes, reaction process 2 is preferred.

Production of N-[N-[3-(3-hydroxy-4-methoxyphenyl)-3-methylbutyl]-L-α-aspartyl]-L-phenylalanine 1-methyl ester from the 3-(3-hydroxy-4-methoxyphenyl)-3-methylbutyl aldehyde can be achieved by reductively alklyating the aldehyde with an α-L-aspartyl-L-phenylalanine methyl ester (aspartame) under a hydrogenation condition (hydrogen addition) to yield the aspartyl dipeptide ester derivative.

In such a reaction, any solvent can be used provided it is inactive with the starting material, a catalyst and a product in the reaction. A homogeneous organic solvent which can dissolve the aspartame and the above described aldehyde, and which is a single solvent of one kind of organic solvent only; a mixture of organic solvents; or a mixed solvent with water may be used.

Examples of such organic solvents include, but not limited to, alcohols, such as methanol, and ethanol, tetrahydrofuran, acetonitrile, and dimethylformamide. From a practical standpoint, alcohol(s) such as methanol or water-containing alcohol(s), such as water-containing methanol are preferred.

If a catalyst is used for hydrogenation (hydrogen addition), then such catalysts can be chosen from, for example, palladium based catalyst, platinum based catalyst, and rhodium based catalyst.

The reductive alkylation reaction can be conducted through hydrogenation (hydrogen addition), and under hydrogen pressure, preferably from about 0.1 to about 1.0 MPa.

The reaction temperature can be chosen so that the reductive alkylation proceeds suitably, for example, to suppress (limit) a secondary reaction and to promote the reaction desired, a temperature range of about 15 to about 50° C. for about 2 to about 72 hours can be used.

The molar ratio of aspartame to the starting aldehyde can be from about 0.5 to about 1.5 moles of the aspartame per 1 mole of the aldehyde.

The Friedel-Crafts reaction, which uses a hydroxyl-protective derivative of 2-methoxy phenol represented by formula (1) is known and described in the Journal of the Agricultural Food Chemistry (1997), vol. 45, No. 6, page 2047–2054. Therefore, according to this known process, as shown in the reaction process 3 below, a phthalic anhydride and a 2-methane sulfonyloxy anisole are subjected to a Friedel-Crafts reaction in the presence of aluminum chloride yielding methane sulfonic acid ester, which in turn is hydrolyzed to obtain a 2-(3-hydroxy-4-methoxybenzoyl)benzoic acid.

In this process, it is possible to introduce an acyl group at the para-position to a methoxy group located on the benzene ring, but the yields are low. Accordingly, it is difficult to estimate the yield obtained in the Friedel-Crafts reaction with a 3-methylcrotonic acid and particularly, whether it proceeds to obtain high yields of the target product. However, in this known reaction the butyric acid derivative, which is extremely useful as an intermediate for producing the sweeteners described herein, were not suggested.

Reaction Process 3

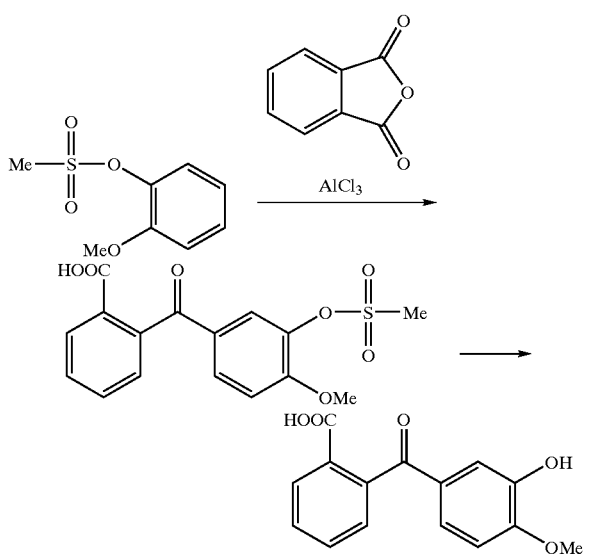

A similar process, as described in International Patent Publication WO99/18064, provides that a compound having a benzene ring with an electron donating group (electron releasing group) at the ortho-position to a phenolic hydroxyl group located on the benzene ring, the phenolic hydroxyl group is protected by a sulfonic acid ester, and then an electrophilic reagent is reacted with the ester, whereby the reaction proceeds at the para-position to the electron donating group on the benzene ring. However, in the Friedel-Crafts reaction described in WO99/18064, substances such as acid chloride, acid anhydride, 3-chloro-2-methylpropene, and the like, which are all known are reacted in the presence of an acid.

On the other hand, it is difficult to say that a process using a 3-methylcrotonic acid as an electrophilic reagent in the Friedel-Crafts reaction was not well-established. For example, in a process for reacting an anisole with a 3-methylcrotonic acid in the presence of aluminum chloride (as in the present invention) to synthesize a 3-(4-methoxyphenyl)-3-methylbutyric acid, (which is described in the Journal of Organic Chemistry (1972), vol. 37, No. 36, p. 825–836), the 3-(4-methoxyphenyl)-3-methylbutyric acid obtained gives a yield of about 10% to the 3-methylcrotonic acid employed, and therefore this process is not particularly useful with respect to the yield. Therefore, it was quite surprising that the crotonic acid derivative as found in the present invention, can be used to produce the objective derivative at an extremely high yield. In the same manner as above, from the above described known process, the butyric acid derivative obtained in the present invention, which is extremely useful as an intermediate for producing the sweeteners described herein, was not suggested.

Reaction Process 4

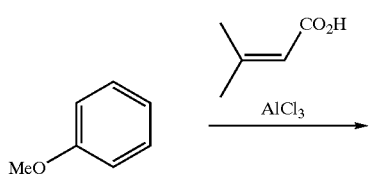

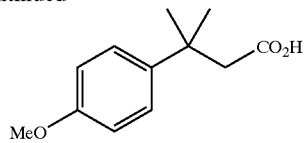

Having generally described this invention, a further understanding can be obtained by reference to certain specific examples which are provided herein for purposes of illustration only, and are not intended to be limiting unless otherwise specified.

EXAMPLES

Example 1

Synthesis of 3-(3-Methanesulfonyloxy-4-methoxyphenyl)-3-methylbutyric Acid

To sodium hydroxide in the pellet form (70.8 g), toluene (200 ml) and distilled water (350 ml) were added to dissolve completely the solid material. Subsequently, 2-methoxy phenol (200 g) was added dropwise thereto over a period of 30 minutes, and then methanesulfonyl chloride (184.4 g) was added dropwise thereto at room temperature over a period of 1 hour, and thus obtained mixture as it is, was stirred for 10 hours. Subsequently, the organic layer was separated, and the obtained solution as it is, was subjected to a step for removal of the solvent by distillation under reduced pressure. Thus obtained residue was subjected a step for distillation under reduced pressure of 1.1 to 1.4 mmHg (146.7 to 186.7 Pa), to obtain unreacted 2-methoxy phenol (64 g) and 2-methanesulfonyloxy anisole (223.6 g, yield: 68%).

A mixture of 2-methanesulfonyloxy anisole (4.0 g) and 3-methylcrotonic acid (1.0 g) was stirred, and to the thus mixed solution, 95% sulfuric acid (1.0 g) was added, and the mixture was stirred for 12 hours at 70° C. The obtained reaction solution was cooled to about room temperature, and then distilled water was added thereto to stop the reaction. The reaction solution was extracted with the use of diethyl ether, and the organic layer separated was further extracted with the use of one normal (1N) sodium hydroxide aqueous solution. Subsequently, 6N hydrochloric acid (HCl) solution was further added to the aqueous layer separated, to acidify the solution. The obtained aqueous solution was extracted with diethyl ether twice, and thereafter, thus obtained organic layer was concentrated under reduced pressure to obtain a crude 3-(3-methanesulfonyloxy-4-methoxyphenyl)-3-methylbutyric acid (1.1 g; yield in the NMR: 33.8% to the 3-methylcrotonic acid).

$^1$H NMR (CDCl$_3$): δ: 1.44 (s, 6H), 2.60 (s, 2H), 3.15 (s, 3H), 3.87 (s, 3H), 6.94 (d, J=8.5 Hz, 1H), 7.22–7.31 (m, 2H). ESI-MS:

Calculation: C$_{13}$H$_{18}$O$_6$S=302.34, Analysis: 301.2 (MH$^-$).

Example 2

Synthesis of 3-(3-Hydroxy-4-methoxyphenyl)-3-methylbutyric Acid

A mixture of 2-methanesulfonyloxy anisole (240 g) and 3-methylcrotonic acid (39 g) was stirred, and to the thus mixed solution, aluminum chloride (104 g) was added, and the mixture was stirred for 5 hours at 70° C., and then further stirred for 2 hours at 100° C. The obtained solution was cooled to about room temperature, and then 6N hydrochloric acid (HCl) solution (390 ml) was added thereto, and the mixture was stirred for 3 hours vigorously. The solution obtained was extracted with the use of methylene chloride (300 ml), and the organic layer separated was further extracted with the use of two normal (2N) sodium hydroxide (NaOH) aqueous solution (400 ml). Subsequently, 6N hydrochloric acid (HCl) solution was further added to the aqueous layer separated, to acidify, the solution. The obtained aqueous solution was extracted with methylene chloride (300 ml) twice, and thereafter, thus obtained organic layer was concentrated under reduced pressure to obtain a residue. Subsequently, to the residue thus obtained, 6N NaOH aqueous solution (300 ml) was added, and the mixture was stirred for 4 hours at 100° C. for mixing. The obtained reaction solution was cooled to a room temperature, and then 6N HCl solution was added thereto, to acidify the solution. The obtained solution was extracted with ethyl acetate. From the organic solution separated, the solvent therein was removed by distillation under reduced pressure, and thereafter, the obtained crude crystals were recrystallized with toluene to obtain 3-(3-hydroxy-4-methoxyphenyl)-3-methylbutyric acid as objective (33.2 g; yield: 37.9% to the 3-methylcrotonic acid).

$^1$H NMR (CDCl$_3$): δ: 1.42 (s, 6H), 2.60 (s, 2H), 3.86 (s, 3H), 6.78 (d, J=8.5 Hz, 1H), 6.84 (dd, J=2.2, 8.5 Hz, 1H), 6.95 (d, J=2.2 Hz, 1H). ESI-MS:

Calculation: C$_{12}$H$_{16}$O$_4$=224.3, Analysis: 223.2 (MH$^-$).

Example 3

Synthesis of 3-(3-Hydroxy-4-methoxyphenyl)-3-methylbutyl Aldehyde

Into a chemical reactor for hydrogen addition (hydrogenation) under elevated pressure, 3-(3-hydroxy-4-methoxyphenyl)-3-methylbutyric acid (13.6 g), pivalic acid anhydride (22.8 g) and acetone (100 ml) were filled, and thereafter the mixture was bubbled with nitrogen gas for 30 minutes to substitute nitrogen gas completely for the gas in the system of reaction, whereby the system was filled with nitrogen gas. Palladium acetate (137 mg) and tetrahydrofuran solution (5 ml) of tri(p-tolyl) phosphine (930 mg) prepared previously, were added thereto, and then the mixture was stirred under hydrogen pressure of 5 MPa at 80° C. for 24 hours. From the obtained reaction solution, acetone was removed by vaporization. The remaining residue was subjected to a purification process with the use of a column chromatography to obtain 3-(3-hydroxy-4-methoxyphenyl)-3-methylbutyl aldehyde (10.2 g, yield: 80%).

$^1$H NMR (CDCl$_3$): δ: 1.41 (s, 6H), 2.61 (d, J=3.0 Hz, 2H), 3.87 (s, 3H), 6.72–6.84 (m, 2H), 6.98 (d, J=1.9 Hz, 1H), 9.49 (t, J=3.0 Hz, 1H). ESI-MS: Calculation: C$_{12}$H$_{16}$O$_3$=208.3, Analysis: 207.2 (MH$^-$).

Example 4

Synthesis of N-[N-[3-(3-Hydroxy-4-methoxyphenyl)-3-methylbutyl]-L-α-aspartyl]-L-phenylalanine 1-Methyl Ester A 3-(3-hydroxy-4-methoxyphenyl)-3-methylbutyl aldehyde (6.677 g, 25.2 mmol) was dissolved in 80% methanol aqueous solution (272 ml), and aspartame (8.446 g, 27.8 mmol) was added thereto to prepare a slurry solution. 10% Palladium on activated carbon in the water content of 50% (2.86 g) was added thereto under nitrogen stream, and then hydrogen was substituted for the gas inside the system of reaction, and the mixture obtained as it is, was stirred for 24 hours at 25° C. After the substitution of nitrogen for the gas in the system of reaction, the catalyst was removed by filtration. Water (190 ml) was added to the filtrate, and the solution was extracted with toluene (250 ml) twice. The methanol/water layer separated was concentrated under reduced pressure to about one second (½) of the amount thereof (half as much) by weight, and then, the solution was cooled gradually from 75° C. to 5° C. to precipitate crystals. The crystals separated were dissolved in 50% methanol aqueous solution (260 ml) at 75° C. and cooled to 5° C. to precipitate crystals. The crystals were dried under reduced pressure to obtain N-[N-[3-(3-hydroxy-4-methoxyphenyl)-3-methylbutyl]-L-α-aspartyl]-L-phenylalanine 1-methyl ester (8.46 g, 17.1 mmol, yield: 67.6% to the aldehyde) as the white crystals. The purity in the HPLC was 98%.

The physical data on the N-[N-[3-(3-hydroxy-4-methoxyphenyl)-3-methylbutyl]-L-α-aspartyl]-L-phenylalanine 1-methyl ester are in the followings.

$^1$H NMR (DMSO-d$_6$): δ: 1.14 (brs, 6H), 1.54–1.68 (m, 2H), 2.04–2.22 (m, 3H), 2.24–2.34 (dd, 1H), 2.84–2.94 (dd, 1H), 3.00–3.08 (dd, 1H), 3.31–3.36 (m, 1H), 3.59 (s, 3H), 3.71 (s, 3H), 4.46–4.55 (m, 1H), 6.60–6.65 (dd, 1H), 6.73 (s, 1H), 6.80 (d, 1H), 7.10–7.28 (m, 5H), 8.45 (d, 1H), 8.75 (brs, 1H).

ESI-MS: 487.3 (MH$^+$).

Effect of Invention

By using a 3-(3-hydroxy-4-methoxyphenyl)-3-methylbutyl aldehyde or a 3-(3-hydroxy-4-methoxyphenyl)-3-methylbutyric acid used as an intermediate for the production in the present invention, and in case of the butyric acid derivative, the butyric acid derivative is converted into the aldehyde corresponding to the butyric acid derivative, and the aldehyde derivative is subjected to a process for reductive alkylation reaction with an aspartame, whereby the N-[N-[3-(3-hydroxy-4-methoxyphenyl)-3-methylbutyl]-L-α-aspartyl]-L-phenylalanine 1-methyl ester important as a sweetener having a high potency of sweetness can be easily produced industrially and efficiently.

The aldehyde derivative and butyric acid derivative described above are novel compounds, and these compounds can be easily and efficiently produced through a process which comprises:

reacting a hydroxyl-protective derivative of 2-methoxy phenol where the hydroxyl group in the 2-methoxy phenol is protected in the form of a sulfonic acid ester thereof with a 3-methylcrotonic acid in the presence of an acid;

removing a moiety of the protecting group therein described above by means of hydrolysis or the like to convert it into a hydroxyl group; and further converting the carboxylic acid obtained into an aldehyde, where necessary.

Therefore, owing the process in the present invention, the sweetener with a high potency of sweetness described above can be produced industrially and advantageously.

Some novel compounds useful as intermediates for the production thereof, such as the aldehyde derivative, the butyric acid derivative and the like described above, are provided.

The present application claims priority to Japanese Patent Application JP 11-328100 filed on Nov. 18, 1999, the contents of which are incorporated herein by reference.

Obviously, numerous modifications and variations on the present invention are possible in light of the above teachings. It is therefore to be understood that within the scope of the appended claims, the invention may be practiced otherwise than as specifically described herein.

What is claimed is:

1. A compound of formula (3):

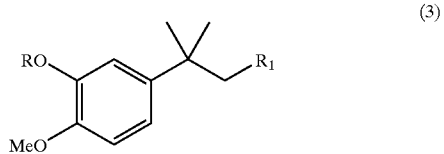

wherein R is a sulfonyl type protecting group; Me is a methyl group; and $R_1$ is a carboxyl group, a formyl group or a hydroxymethyl group.

2. The compound as defined in claim 1, wherein R is a protecting group represented by the formula: —SO$_2$—R', R' is selected from the group consisting of an unsubstituted straight chain alkyl group having 1 to 10 carbon atoms; an unsubstituted branched chain alkyl group having 1 to 10 carbon atoms, a substituted straight chain alkyl group having 1 to 10 carbon atoms; a substituted branched chain alkyl group having 1 to 10 carbon atoms; an unsubstituted aryl group having 6 to 15 carbon atoms, a substituted aryl group having 6 to 15 carbon atoms; an unsubstituted aralkyl group having 7 to 20 carbon atoms; and a substituted aralkyl group having 7 to 20 carbon atom.

3. The compound as defined in claim 1, wherein said alkyl group is fluorinated.

4. The compound as defined in claim 1, wherein said aralkyl group is fluorinated.

5. The compound as defined in claim 1, wherein $R_1$ is a carboxyl group, and

R is selected from the group consisting of a benzene sulfonyl group, a p-toluene sulfonyl group, a p-bromobenzene sulfonyl group, a p-nitrobenzene sulfonyl group, a methane sulfonyl group, an ammonio-alkane sulfonyl group, a trifluoromethane sulfonyl group, a nonafluorobuthane sulfonyl group, and a 2,2,2-trifluoroethane sulfonyl group.

6. The compound as defined in claim 1, wherein $R_1$ is a carboxyl group, and

R is selected from the group consisting of a methane sulfonyl group, a trifluoromethane sulfonyl group, and a p-toluene sulfonyl group.

7. The compound as defined in claim 1, wherein $R_1$ is a carboxyl group, and R is a methane sulfonyl group.

8. 3-(3-methanesulfonyloxy-4-methoxyphenyl)-3-methylbutyric acid.

* * * * *

UNITED STATES PATENT AND TRADEMARK OFFICE
CERTIFICATE OF CORRECTION

PATENT NO.    : 6,693,214 B2
DATED         : February 17, 2004
INVENTOR(S)   : Kawahara et al.

It is certified that error appears in the above-identified patent and that said Letters Patent is hereby corrected as shown below:

Title page,
Item [30], Foreign Application Priority Data, should read:
-- [30]        Foreign Application Priority Data
   Nov. 18, 1999      (JP) ………………….. 11-328100 --

Signed and Sealed this

Eighteenth Day of May, 2004

JON W. DUDAS
*Acting Director of the United States Patent and Trademark Office*